(12) United States Patent
Gemmel et al.

(10) Patent No.: US 10,653,386 B2
(45) Date of Patent: May 19, 2020

(54) MOBILE X-RAY MACHINE

(71) Applicant: SIEMENS HEALTHCARE GMBH, Erlangen (DE)

(72) Inventors: Alexander Gemmel, Erlangen (DE); Gerhard Kleinszig, Forchheim (DE); Wei Wei, Forchheim (DE); Markus Weiten, Nuremberg (DE)

(73) Assignee: Siemens Healthcare GMBH, Erlangen (DE)

( * ) Notice: Subject to any disclaimer, the term of this patent is extended or adjusted under 35 U.S.C. 154(b) by 179 days.

(21) Appl. No.: 15/514,103

(22) PCT Filed: Sep. 16, 2015

(86) PCT No.: PCT/EP2015/071160
§ 371 (c)(1),
(2) Date: Mar. 24, 2017

(87) PCT Pub. No.: WO2016/046032
PCT Pub. Date: Mar. 31, 2016

(65) Prior Publication Data
US 2017/0290559 A1    Oct. 12, 2017

(30) Foreign Application Priority Data

Sep. 25, 2014    (DE) .......................... 10 2014 219 436

(51) Int. Cl.
A61B 6/00    (2006.01)
A61B 6/08    (2006.01)

(52) U.S. Cl.
CPC ................ *A61B 6/587* (2013.01); *A61B 6/08* (2013.01); *A61B 6/4405* (2013.01); *A61B 6/4441* (2013.01); *A61B 6/469* (2013.01); *A61B 6/545* (2013.01); *A61B 6/547* (2013.01); *A61B 6/5241* (2013.01)

(58) Field of Classification Search
CPC ....... A61B 6/08; A61B 6/4405; A61B 6/4441; A61B 6/469; A61B 6/5241; A61B 6/545; A61B 6/547; A61B 6/587
See application file for complete search history.

(56) References Cited

U.S. PATENT DOCUMENTS

| 7,016,457 | B1 * | 3/2006 | Senzig | A61B 6/032 378/116 |
| 7,500,783 | B2 * | 3/2009 | Kalender | A61B 6/032 378/197 |
| 2001/0022834 | A1 * | 9/2001 | Graumann | A61B 6/4405 378/198 |

(Continued)

FOREIGN PATENT DOCUMENTS

| DE | 102006044783 A1 | 4/2008 |
| DE | 102006055133 A1 | 6/2008 |

(Continued)

*Primary Examiner* — David J Makiya
*Assistant Examiner* — Soorena Kefayati
(74) *Attorney, Agent, or Firm* — Laurence Greenberg; Werner Stemer; Ralph Locher

(57) ABSTRACT

An apparatus and a method are provided for positioning an x-ray machine having an x-ray source and a detector. A second X-ray image is recorded once an x-ray apparatus has been positioned by using information of an alignment point in a first x-ray image.

10 Claims, 2 Drawing Sheets

(56) References Cited

U.S. PATENT DOCUMENTS

| | | | | |
|---|---|---|---|---|
| 2001/0027263 | A1* | 10/2001 | Zylka | A61B 6/12 600/9 |
| 2002/0099284 | A1* | 7/2002 | Herrmann | A61B 6/08 600/407 |
| 2005/0053200 | A1* | 3/2005 | Sukovic | A61B 90/36 378/210 |
| 2006/0293582 | A1* | 12/2006 | Jensen | A61B 6/08 600/407 |
| 2007/0211847 | A1* | 9/2007 | Graumann | A61B 6/102 378/15 |
| 2007/0237287 | A1* | 10/2007 | Sukovic | A61B 6/032 378/4 |
| 2007/0248206 | A1* | 10/2007 | Sukovic | A61B 6/4405 378/4 |
| 2008/0075225 | A1* | 3/2008 | Kalender | A61B 6/032 378/20 |
| 2008/0118036 | A1* | 5/2008 | Jensen | A61B 6/4441 378/198 |
| 2008/0161684 | A1* | 7/2008 | Li | A61B 5/06 600/426 |
| 2009/0274271 | A1* | 11/2009 | Pfister | A61B 6/12 378/62 |
| 2010/0157041 | A1* | 6/2010 | Klaiman | A61B 6/481 348/77 |
| 2011/0305320 | A1* | 12/2011 | Suuronen | A61B 6/00 378/98.5 |
| 2012/0057674 | A1* | 3/2012 | Zhang | A61B 5/7285 378/62 |
| 2012/0069968 | A1* | 3/2012 | Core | A61N 5/1049 378/206 |
| 2012/0099697 | A1* | 4/2012 | Helm | A61B 6/02 378/4 |
| 2012/0099778 | A1* | 4/2012 | Helm | A61B 6/4476 382/132 |
| 2012/0281812 | A1* | 11/2012 | Noda | A61B 6/4233 378/62 |
| 2013/0083894 | A1* | 4/2013 | Niebler | A61B 6/4441 378/62 |
| 2013/0163721 | A1* | 6/2013 | Koh | A61B 6/06 378/62 |
| 2013/0243160 | A1* | 9/2013 | Graumann | A61B 6/54 378/91 |
| 2013/0287171 | A1* | 10/2013 | Hibino | A61B 6/4405 378/62 |
| 2015/0085986 | A1* | 3/2015 | Dinse | A61B 6/10 378/98 |
| 2015/0110245 | A1* | 4/2015 | Kim | A61B 6/48 378/62 |
| 2015/0117608 | A1* | 4/2015 | Lytle | G06T 7/33 378/62 |
| 2015/0124940 | A1* | 5/2015 | Kim | A61B 6/547 378/189 |
| 2015/0190204 | A1* | 7/2015 | Popovi | A61B 34/20 600/424 |
| 2015/0305703 | A1* | 10/2015 | Kim | A61B 6/467 378/62 |

FOREIGN PATENT DOCUMENTS

| | | |
|---|---|---|
| EP | 1016375 A1 | 7/2000 |
| WO | 2007126932 A1 | 11/2007 |

\* cited by examiner

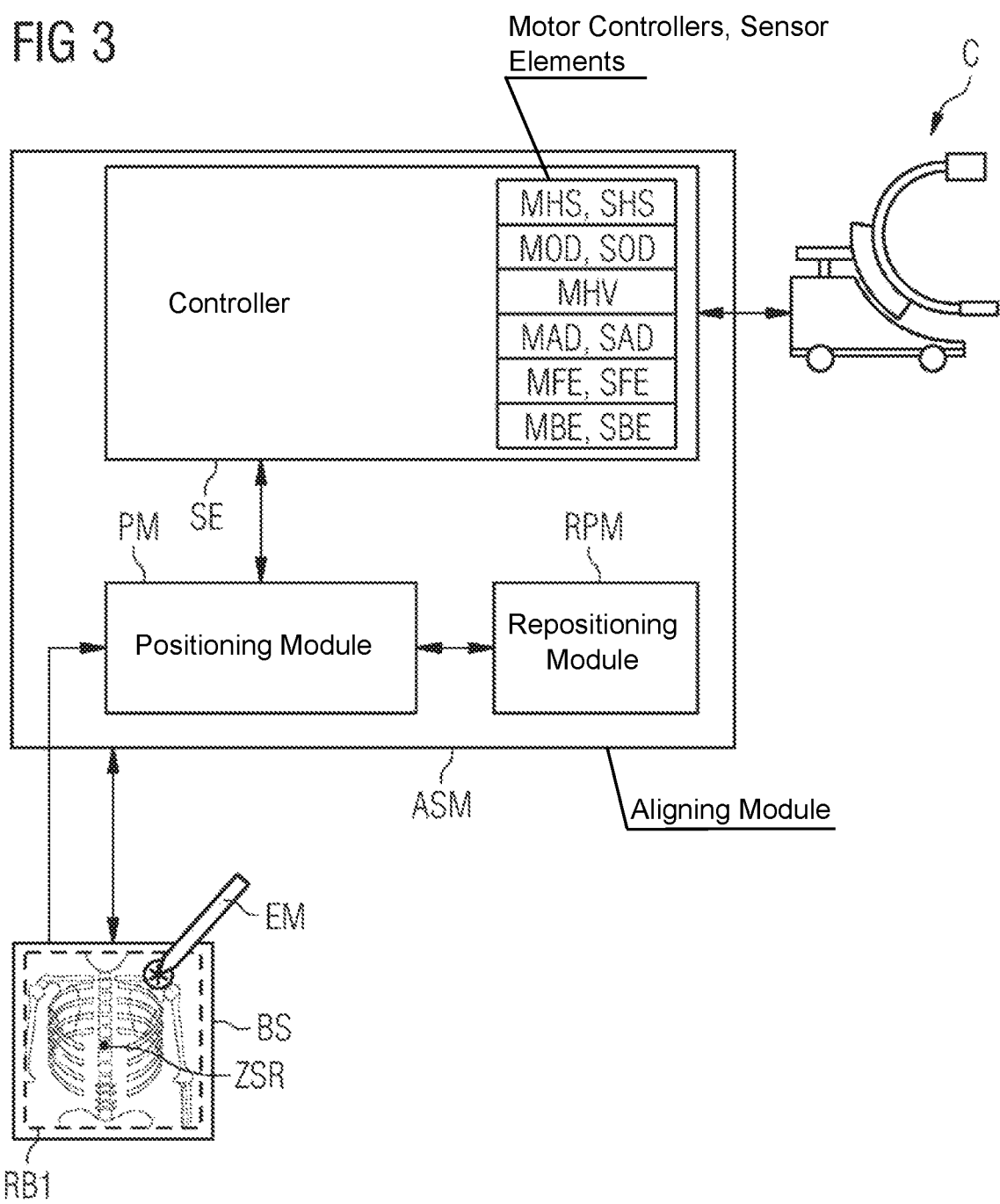

MOBILE X-RAY MACHINE

BACKGROUND OF THE INVENTION

Field of the Invention

In addition to a platform equipped with controllable movement elements, mobile x-ray machines have controllable holding elements for an x-ray system which, for example, is arranged at a C-arm. By way of example, wheels could be used as controllable movement elements. The individual controllable holding elements, by means of which the x-ray source and the detector of the x-ray system are alignable onto a region of an object to be x-rayed, are e.g. a rotatable and height-adjustable lifting column and connecting elements between lifting column and C-arm. The C-arm has such a functional connection with the connecting elements that both an orbital rotation and an angular rotation can be carried out thereby.

Positioning and/or alignment, and also repositioning, of the mobile x-ray machine is carried out according to the instructions of the treating medical practitioner, who wishes to create x-ray images of specific treatment regions, for example for developing a treatment plan and/or making the latter more precise.

For a first x-ray image, or a plurality of x-ray images, the movement elements and holding or connecting elements of the mobile x-ray machine are actuatable in such a way that the movement elements of the displaceable platform and the movement elements of the connecting elements, together or on their own, may be guided between chassis and C-arm. The movement elements and connecting elements may be adjusted electronically, semi-electronically or manually.

The medical practitioner may gather an overview of the treatment area put into focus by him using a first x-ray image, which may also be referred to as an overview x-ray recording. However, for a verified treatment plans already discussed above, further x-ray images of the treatment area or a region of interest have to be taken under certain circumstances. However, positioning and aligning the x-ray source of the x-ray system for answering a specific medical question is often difficult.

After imaging the region of interest in the x-ray image, the mobile x-ray machine is removed again from the operating table or from the region of interest by hand and temporarily parked at a different position in the operating theater or treatment room which is not frequented by the surgical staff in order then, in line with the advance of the intervention, for the x-ray machine to once again be repositioned at the operating table by hand for the purposes of making one or more x-ray recordings.

Until the medical problem is solved, the mobile x-ray machine or the x-ray system, under certain circumstances, has to be repositioned or aligned multiple times by hand in order to image a plurality of x-ray images of a specific region of interest.

Currently, the positioning and, in particular, the repositioning of the mobile x-ray machine is carried out e.g. by an assistant in line with the instructions of the surgeon. The surgeon predetermines the projection directions of the x-ray source of the x-ray system for the acquisition of necessary x-ray images and corrects the positioning and/or alignment of such an x-ray source, and possibly the projection direction thereof as well, iteratively on the basis of the created x-ray images until a meaningful x-ray image is present.

In addition to a great time outlay for accurate positioning or repositioning of the mobile x-ray machine, the previous procedure harbors the further disadvantage of the patient and the surgical team being exposed to additional radiation exposure as a result of a multiplicity of x-ray images.

SUMMARY OF THE INVENTION

The invention is based on the object of specifying a further apparatus and an associated method for positioning an x-ray machine.

The object is achieved by an apparatus for positioning an x-ray machine embodied with an x-ray source and a detector, in which provision is made for an aligning module for positioning the x-ray machine, wherein a first x-ray image is matched in a 3D data record created preoperatively or intraoperatively and at least one alignment point or a trajectory in the 3D data record can be noted for the purposes of forming at least one second x-ray image. This object is also achieved by a method for positioning an x-ray machine embodied with an x-ray source and a detector, in which an alignment of the x-ray source is carried out according to the prescription of at least one alignment point or a trajectory matched in a preoperative or intraoperative 3D data record and noted in a first x-ray image and at least one second x-ray image is created.

Provision is made of an aligning module for positioning the x-ray source in the apparatus and in the method for the purposes of positioning an x-ray source arranged at an x-ray system, wherein the x-ray source is aligned for a second x-ray image according to the prescription of an alignment point which is noted or marked in a first x-ray image.

The invention harbors the advantage of the x-ray source being able to be positioned or repositioned on the basis of a first x-ray image.

The invention harbors the advantage of or iterative positioning and repositioning cycles with the mobile C-arm being dispensed with and is determinable as a result of a single positioning or repositioning specification within an already made first x-ray image.

The invention harbors the advantage that a first x-ray image is also reconstructable on the basis of a 3D data record of an object created from a multiplicity of x-ray recordings and that the x-ray source may be positioned or repositioned on account of the reconstructed first x-ray image.

The invention harbors the advantage that movement vectors or coordinates for the x-ray machine to be controlled are ascertainable on account of a marking which is detectable and undertaken in a first x-ray recording.

Below, the subject matter of the invention will be explained in more detail on the basis of drawings.

BRIEF DESCRIPTION OF THE SEVERAL VIEWS OF THE DRAWING

FIG. 3 shows a detailed view for controlling the mobile x-ray machine.

DESCRIPTION OF THE INVENTION

In the subject matter of the apparatus and the associated method, a second x-ray image is made after positioning an x-ray machine on the basis of the prescription of an alignment point in a first x-ray image.

Figure 1:
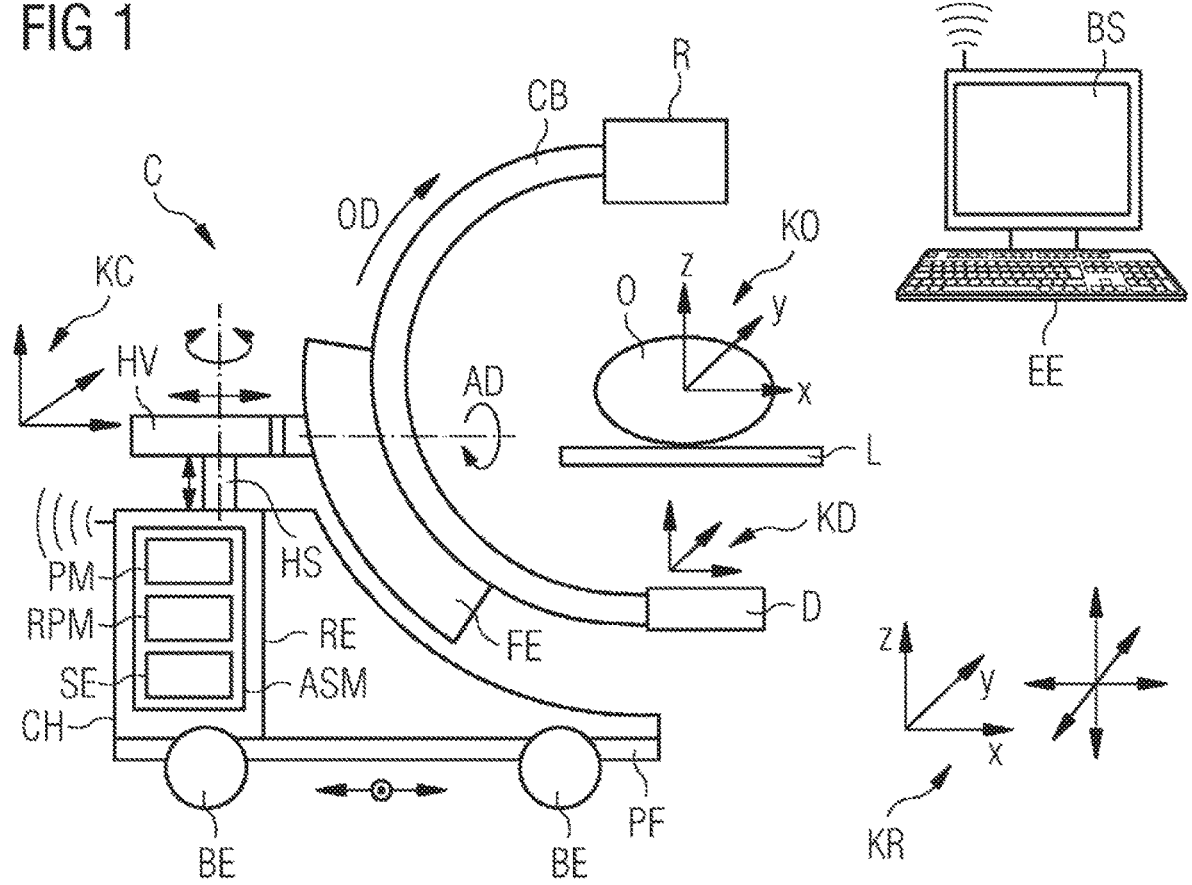
FIG. 1 shows a schematic illustration of a mobile x-ray machine.

FIG. 1 schematically reproduces an x-ray machine, in particular a mobile x-ray machine comprising a C-arm CB. An x-ray source R and a detector D are arranged at the open ends of the C-arm CB. This mobile C-arm CB comprises a displaceable platform PF provided with movement elements BE. By way of example, the movement elements BE may be controllable wheels such as spherical wheels, rotatable running wheels or omni wheels. A chassis CH is arranged on the platform PF. Firstly, the attachment of the movable C-arm and, secondly, the computing unit RE required for controlling the movable C-arm are integrated into this chassis CH. Inter alia, a positioning module PM, a repositioning module RPM and an aligning module ASM comprising a controller SE are integrated into the computing unit RE. The holding elements, which are arranged between chassis CH and C-arm CB and which may also be referred to as connecting elements, are subdivided into a lifting column HS and a horizontal connecting element HV comprising a guiding unit FE for the semicircular C-arm CB. The horizontal connecting element HV and the lifting column HS are movably mounted in each case over the axes plotted in this sketch. Lifting column HS and horizontal connecting element HV are each embodied with positioning means. The entire C-arm can be lifted and lowered by means of the lifting column HS. The cross bracing arranged on the lifting column HS serves for the horizontal alignment of the C-arm CB. Likewise, the lifting column HS and the horizontal connecting element HV are respectively embodied in such a way that a rotation of the lifting column HS or a rotation of the connecting element HV about the axes extending therein is possible. The rotation about the horizontally extending axis in the connecting element HV causes an angular rotation AD of the C-arm. A displacement of the C-arm along the curved guiding unit FE results in an orbital rotation OD of the C-arm CB. Below, the individual motorizable elements such as movement elements BE, lifting column HS, horizontal connecting element HV or guiding unit FE are also referred to as positioning means. Stored in the computing unit RE are, firstly, the coordinates of a first coordinate system KC assigned to the C-arm CB, a second coordinate system KD assigned to the detector D, and a third coordinate system KO assigned to an object O placed on a couch L between the x-ray source R and the detector D. Moreover, the computing unit RE even has access to a fourth coordinate system KR. The fourth coordinate system KR is in each case assigned to a room in which the mobile C-arm CB is situated. These coordinates of the first to fourth coordinate systems KC, KD, KO, KR may be assigned, respectively, to determine a first x-ray image RB1 and a second x-ray image RB2 such that, by means of arbitrary coordinate transforms between the individual coordinate systems KC, KD, KO and KR, it is possible to calculate a positioning and/or an alignment and a repositioning of the C-arm CB. By means of an input means, such as a keyboard EE or an electronic marking pen EM, the alignment of the C-arm CB or of the x-ray source R may be predetermined, for example, on a monitor BS on the basis of at least one marking in the form of an alignment point AP in a first x-ray image RB1 which, for example, is also imaged on the monitor BS. If a plurality of alignment points APn are noted in the first x-ray image RB1, the individual alignment points APn are worked through in succession in accordance with their input sequence and a second x-ray image RB2 is in each case produced in this respect.

Figure 2:
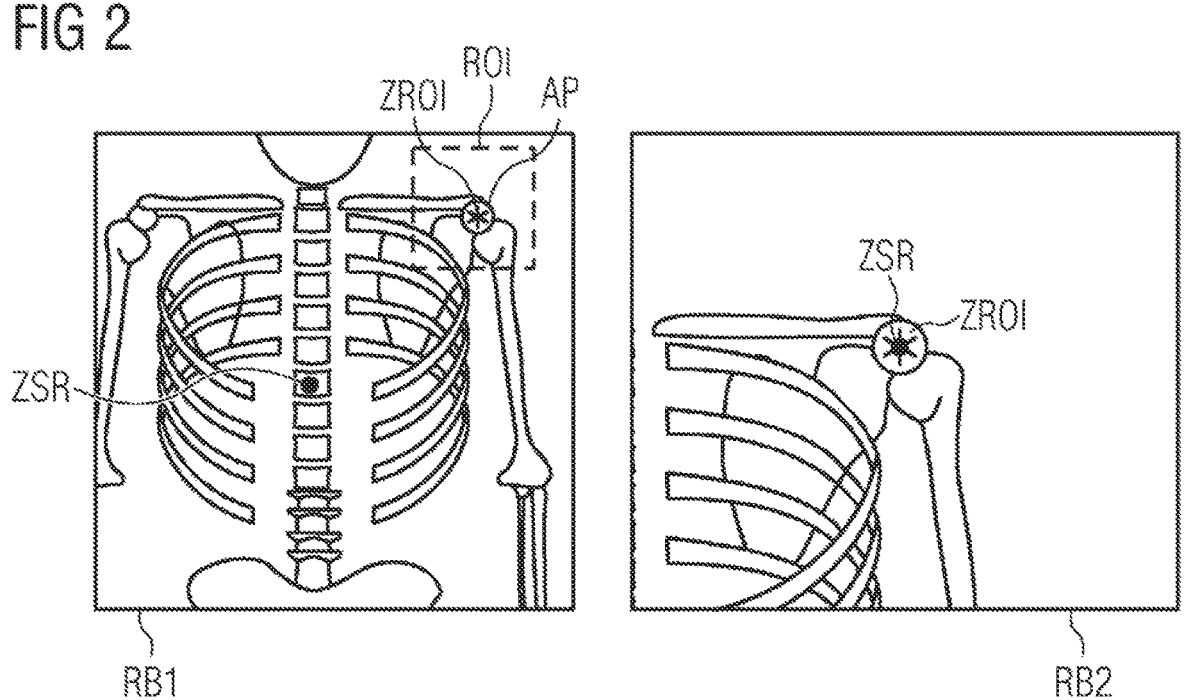
FIG. 2 shows a first x-ray image and a second x-ray image.

FIG. 2 reproduces a first x-ray image RB1 and a second x-ray image RB2. The first x-ray image RB1 may likewise be referred to as an overview x-ray image. By specifying a region of interest, an alignment of the x-ray system is prepared from the overview x-ray image in such a way that, by means of an input means EM or a keyboard EE, an alignment point AP in the form of a cursor point is predetermined in a first x-ray image RB1 visualized on a visualization unit BS. By way of example, the visualization unit may be a tablet or a monitor. The control pulses required for controlling the positioning means in order to bring the x-ray source R into the desired alignment are converted on the basis of the alignment point AP in the first x-ray image RB1 and the assignable coordinate systems KC, KD, KO, KR. The alignment point AP predetermined in the first x-ray image RB1, which may also be referred to as a center of a region of interest ZROI, forms the location of the principal ray ZSR, which is situated in the image center thereof, in the second x-ray image RB2. When the alignment point AP is set in the first x-ray image RB1, there also may be, at the same time, a tilt of the image plane about an x-ray focal point to be set. In the described example, the x-ray focal point lies in the alignment point AP in the image plane. In a further embodiment variant, there is also a local change of the x-ray focal point along a straight line passing through the alignment point AP. An orbital rotation OD and/or an angular rotation AD of the C-arm CB may be carried out for the purposes of tilting the image plane. Using this configuration, the surgeon may additionally make the direction of view onto the center of the region of interest ROI more precise.

In a further embodiment variant, a first x-ray image RB1 may be created by reconstruction from a created 3D data record. The 3D data record may be created by a multiplicity of x-ray recordings of an object made preoperatively or intraoperatively, for example during a circular-arc-shaped trajectory. Using this 3D data record, the treating medical practitioner may set a slice plane for creating a first x-ray image RB1 through the object O. This created first x-ray image RB1 is then imaged on the monitor BS. Then, a more precise alignment for a region of interest ROI in a second x-ray recording RB2 may be predetermined on this first x-ray image RB1. This prescription may be carried out either manually or electronically. In the case of an electronic prescription, a specific landmark, such as the spinal column, may be identified and one or more alignment points may be set on the vertebrae for the purposes of aligning the x-ray source for e.g. a series of second x-ray images RB2n. In a further embodiment variant, the first x-ray image RB1 may be matched in a preoperative or intraoperative 3D data record and at least one alignment point AP or a trajectory may be noted in the 3D data record. This is accompanied by the advantage that the image data, the coordinates thereof or the alignment of the 2D x-ray image RB1 may be retrieved in the 3D data record and an alignment of the x-ray machine C may be determined for a second x-ray image RB2 within the 3D data record.

FIG. 3 reproduces a schematic illustration of an apparatus for aligning an x-ray source R and/or a detector D. Inter alia, a positioning module PM, the repositioning module RPM and the controller SE are arranged in the computing unit RE, in which the aligning module ASM is integrated. In the shown apparatus, the positioning data for positioning the x-ray source R arranged at an x-ray machine and/or for positioning a detector D are ascertained by means of an aligning module ASM. For a second x-ray image RB2, the x-ray source R is aligned according to the prescription of an alignment point AP marked in a first x-ray image RB1. The x-ray image denoted by the first x-ray image RB1 may be either an x-ray image or an x-ray image reconstructed from a 3D data field. By way of example, the alignment point AP which is entered in a first x-ray image RB1 on a visualization unit BS, and marked, is read by the controller SE. The control signals for coordinated control of the x-ray machine C are generated in the controller SE for the positioning module PM and repositioning module RPM. These control signals bring about motorized alignment of the x-ray machine C, in particular of the x-ray source R and/or the detector D, on the basis of actual position data and the predetermined coordinates of an alignment point AP deliberately predetermined in a first x-ray image RB1, see also FIG. 2. A comparison of target and actual values is carried out in each case in the positioning module PM between the current alignment and a desired alignment of the x-ray source R, and the x-ray source R brings about by a singular actuation of the motorizable positioning means BE, HS, HV, FE, CB or by inclusion of a multiplicity of motorizable positioning means BE, HS, HV, FE, CB. The x-ray source R is aligned in such a way that an alignment point AP in the region of interest ROI, deliberately selected in a first x-ray image RB1, lies approximately centrally in a second x-ray image RB2. The alignment point AP may also lie on the principal ray ZSR of the x-ray source R. Control signals for the individual elements or units are ascertained in the controller SE. The controllable elements or units are listed below. For the purposes of controlling the x-ray source R, the control signals are ascertained for actuating the elements such as lifting column HS, horizontal connecting element HV or for a further guiding unit FE, in each case by a comparison between actual coordinates and target coordinates. Individual motor controllers of positioning means, such as a motor controller MHS of the lifting column HS, a motor controller MHV of the horizontal connecting elements HV, a motor controller MFE for the guiding unit FE, a motor controller MOD for the orbital rotation, a motor controller MAD for the angular rotation and the motor controller MBE for the movement elements BE, may be actuated. The necessary control signals are calculated in the controller SE. The sensor data required for the motor control are queried by way of sensor elements arranged at and/or in the corresponding positioning means. Thus, first sensor elements SHS are integrated in the lifting column HS and there is integration of second sensor elements SOD for the orbital movement of the C-arm CB, third sensor elements SAD for the angular movement of the C-arm CB and fourth sensor elements SFE for guiding elements FE of the C-arm CB arranged between chassis and C-arm CB. The movement of the wheels, for example omni wheels BE, is captured separately by fifth sensor elements SBE. All positioning data for a first x-ray image RB1 and a second x-ray image RB2 are, inter alia, also stored in the repositioning module RPM for the purposes of repositioning the mobile C-arm CB. Controlling the mobile C-arm CB is also triggered by the spatial coordinates for an alignment point AP marked in the first x-ray image RB1, said spatial coordinates being stored in the controller SE. By way of example, the alignment point AP may be entered and imaged in the first x-ray image RB1 by way of a monitor BS embodied with touchscreen elements. The coordinates for the second x-ray image or images RB2 are stored in the repositioning module RPM and positioning module PM arranged in the aligning module ASM. Proceeding from the coordinates of the alignment point AP and the coordinates of the principal ray ZSR of the x-ray source R in respect of a first x-ray image RB1, the position of the x-ray source R is derived for a second x-ray image RB2. The x-ray source R may be aligned for the second x-ray image RB2 by either a singular or a combined actuation of motorizable positioning means BE, HS, HV, FE, CB.

LIST OF REFERENCE SIGNS

R X-ray source
D Detector
C Mobile C-arm
KC First, C-arm coordinate system
KD Second, detector D coordinate system
KO Third, object coordinate system
KR Fourth, room coordinate system
CH Chassis
PF Displaceable platform
BE Movement elements (rotatable running wheels, spherical wheel, omni wheels . . . )
RB1 First x-ray image
RB2 Second x-ray image
RE Computing unit
BS Monitor
EM Input means
AP Alignment point
ASM Aligning module
SE Controller
PM Positioning module
RPM Repositioning module
ZSR Principal ray of the x-ray source
ROI Region of interest
ZROI Center of the region of interest
OD Orbital rotation
AD Angular rotation
HS Lifting column
HV Horizontal connecting element
FE Curved guiding unit
CB C-arm
MHS Motor controller for lifting column HS
SHS First sensor elements for lifting column movement
MHV Motor controller for horizontal connecting element HV
MOD Motor controller for orbital rotation OD
SOD Second sensor elements for orbital rotational movement
MAD Motor controller for angular rotation AD
SAD Third sensor elements for angular rotational movement
MFE Motor controller for guiding elements FE
SFE Fourth sensor elements for guiding elements
MBE Motor controller for movement elements BE
SBE Fifth sensor elements for movement elements

The invention claimed is:
1. An apparatus for positioning an x-ray machine including an x-ray source and a detector, the apparatus comprising:
 a displaceable platform including a moveable x-ray source and/or detector, said platform displaceable by motorized, controllable wheels;
 a computer supported on said platform, said computer including a controller configured to:
  mark, in a first x-ray image in a 3D data record created preoperatively or intraoperatively, at least one alignment point or a trajectory in the 3D data record for forming at least one second x-ray image;
  retrieve from the 3D data record, spatial coordinates of the noted alignment point or trajectory;
  derive spatial coordinates for a position of the x-ray source for a second x-ray image from the received spatial coordinates of the alignment point or trajectory;

generate control signals to bring about motorized alignment of said x-ray source and/or detector, such that said alignment point or trajectory lies approximately centrally in a second x-ray image, said control signals controlling at least one of said motorized, controllable wheels or said moveable x-ray source and/or detector; and said controller additionally configured to control the displacement of said platform supporting the x-ray source, the detector and said computer based on said alignment point or trajectory, by operating said motorized, controllable wheels to move said platform in order to position the x-ray machine.

2. The apparatus according to claim 1, wherein said controller coordinates control of the x-ray machine by ascertaining control signals for motorized alignment of the x-ray machine based on actual position data and predetermined coordinates of the at least one alignment point in the preoperative or intraoperative 3D data record.

3. The apparatus according to claim 1, which further comprises:
at least one of a positioning module or a repositioning module carrying out a comparison of target and actual values between a current alignment and a desired alignment of the x-ray source; and
a single motorizable positioning device being actuated or a plurality of motorizable positioning devices being included for positioning the x-ray source.

4. The apparatus according to claim 1, wherein the x-ray machine has a C-arm disposed on the platform, the x-ray source being disposed at the C-arm.

5. The apparatus according to claim 1, which further comprises a visualization unit for displaying at least one x-ray image by noting the at least one alignment point in the preoperative or intraoperative 3D data record.

6. A method for positioning an x-ray machine according to claim 1, the method comprising the following steps:
aligning the x-ray source according to a prescription of at least one alignment point or a trajectory being matched in a preoperative or intraoperative 3D data record and noted in a first x-ray image; and
creating at least one second x-ray image.

7. The apparatus according to claim 2, wherein said controller is configured to capture the at least one alignment point being predeterminable in the preoperative or intraoperative 3D data record for ascertaining control signals for a motorizable positioning device for aligning the mobile x-ray machine and forming corresponding control signals.

8. The method according to claim 6, which further comprises ascertaining control signals for motorized alignment of the x-ray machine based on actual position data and predetermined coordinates of the at least one alignment point in the preoperative or intraoperative 3D data record.

9. The method according to claim 6, which further comprises:
carrying out a comparison of target and actual values between a current alignment and a desired alignment of the x-ray source; and
positioning the x-ray source by a singular actuation of motorizable elements or by an inclusion of a plurality of motorizable elements.

10. The method according to claim 6, which further comprises aligning the x-ray source according to the prescription of at least one alignment point noted in the preoperative or intraoperative 3D data record and creating the second x-ray image for an alignment point in each case.

* * * * *